United States Patent

Sasse et al.

[11] 4,206,212
[45] Jun. 3, 1980

[54] COMBATING PLANT PATHOGENIC BACTERIA WITH 3-HALOGENO-BENZOTRIAZINE 1-OXIDES

[75] Inventors: Klaus Sasse, Bergisch Gladbach; Peter Kraus, Cologne; Hans Scheinpflug, Leverkusen, all of Fed. Rep. of Germany

[73] Assignee: Bayer Atkiengesellschaft, Leverkusen, Fed. Rep. of Germany

[21] Appl. No.: 936,991

[22] Filed: Aug. 25, 1978

[30] Foreign Application Priority Data

Sep. 10, 1977 [DE] Fed. Rep. of Germany ....... 2740887

[51] Int. Cl.² ............................................... A01N 9/22
[52] U.S. Cl. .................................................. 424/249
[58] Field of Search ......................................... 424/249

[56] References Cited

U.S. PATENT DOCUMENTS 4,067,981  1/1978  Sasse et al. ............................ 424/249

FOREIGN PATENT DOCUMENTS 83869   8/1971  Fed. Rep. of Germany .
45-38280 12/1970 Japan .

Primary Examiner—V. D. Turner

Attorney, Agent, or Firm—Sprung, Felfe, Horn, Lynch & Kramer

[57] ABSTRACT

Plant-pathogenic bacteria are combated with 3-halogeno-benzotriazine 1-oxides of the formula

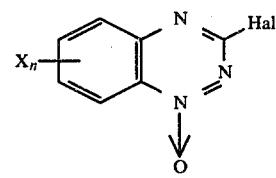

in which
  X each independently is halogen, a nitro group, an alkyl, halogenoalkyl, alkoxy, alkylmercapto or alkylsulphonyl group with up to 4 carbon atoms in each case, a phenoxy radical or a phenylmercapto radical,
  n is an integer from 0 to 4, and
  Hal is chlorine or bromine.

Such compounds are produced by reacting the corresponding 3-hydroxy compounds with thionyl chloride in the presence of dimethylformamide.

7 Claims, No Drawings

COMBATING PLANT PATHOGENIC BACTERIA WITH 3-HALOGENO-BENZOTRIAZINE 1-OXIDES

The present invention relates to the use of certain 3-halogenobenzotriazine 1-oxides, some of which are known, as agents for combating plant bacterioses. Furthermore, it relates to an unobvious process for the preparation of the compounds.

Plant diseases caused by pathogenic bacteria are spreading to an increasing extent, so that in certain regions the economic viability of cultivating some crop plants is now endangered. Important pathogens belong to the family of Pseudomonadaceae, for example *Pseudomonas solanacearum, Pseudomonas lachrymans, Pseudomonas syringae, Xanthomonas citri, Xanthomonas oryzae* and *Xanthomonas vesicatoria,* the family of Enterobacteriaceae, for example *Erwinia amylovora,* and the family of Corynebacteriaceae. The means hitherto available for combating or preventing these diseases are very expensive and at the same time still inadequate. In practice, almost exclusively antibiotics are used for this, the preparation of which is expensive and which in many cases are toxic and, under atmospheric conditions, stable only for a short time.

It has already been disclosed that those benzotriazine 1-oxides which have halogen or an amino, hydrazino, alkoxy or alkylmercapto group in the 3-position have herbicidal, acaricidal and fungicidal properties (in this context see DL Pat. No. 83,869); some have a fungicidal action, for example 3-chloro-benzotriazine 1-oxide and 3,7-dichloro-benzotriazine 1-oxide. However, nothing is known with respect to bactericidal properties.

It has now been found that the 3-halogeno-benzotriazine 1-oxides of the general formula

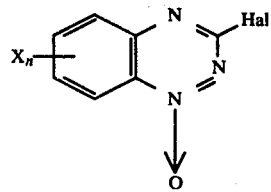

in which
X represents halogen, a nitro group, an alkyl, halogenoalkyl, alkoxy, alkylmercapto or alkylsulphonyl group with up to 4 carbon atoms in each case, a phenoxy radical or a phenylmercapto radical,
n represents 0 or an integer from 1 to 4, the X's being selected independently of one another when n is 2, 3 or 4, and
Hal represents chlorine or bromine,
have a high activity against bacteria which are harmful to plants.

Accordingly, the present invention provides a method of combating plant-pathogenic bacteria which comprises applying to the bacteria, or to a habitat thereof, a compound of the formula (I) alone or in admixture with a diluent or carrier.

Preferably, in the formula (I), each X represents chlorine, bromine, methoxy, phenoxy, methylmercapto, methyl, trifluoromethyl or nitro, n represents 0, 1 or 2 and Hal represents chlorine.

It is to be described as very surprising that the above-mentioned type of compound displays bactericidal actions, since no fungicide hitherto used in practice simultaneously also exhibits bactericidal properties which are useful in practice. The use of these substances as bactericides for plant protection thus represents an enrichment of the art; these substances are also superior to the antibiotics used at present with respect to their degree of action and their stability under atmospheric conditions.

Examples of the active compounds to be used according to the invention are: 3-chloro-benzotriazine 1-oxide, 3-bromo-benzotriazine 1-oxide, 3,5-dichloro-benzotriazine 1-oxide, 3,6-dichloro-benzotriazine 1-oxide, 3,7-dichloro-benzotriazine 1-oxide, 3-bromo-7-chloro-benzotriazine 1-oxide, 3,8-dichloro-benzotriazine 1-oxide, 3,5,7-trichloro-benzotriazine 1-oxide, 3,6,7-trichloro-benzotriazine 1-oxide, 3,5,8-trichloro-benzotriazine 1-oxide, 3-chloro-7-bromo-benzotriazine 1-oxide, 3-chloro-5,7-dibromo-benzotriazine 1-oxide, 3-chloro-7-methoxy-benzotriazine 1-oxide, 3-chloro-7-phenoxy-benzotriazine 1-oxide, 3-chloro-7-methyl-benzotriazine 1-oxide, 3-chloro-7-methylmercapto-benzotriazine 1-oxide, 3-chloro-7-methylsulphonyl-benzotriazine 1-oxide, 3-chloro-7-trifluoromethyl-benzotriazine 1-oxide and 3-chloro-7-nitro-benzotriazine 1-oxide.

The 3-halogeno-benzotriazine 1-oxides of the formula (I) are a type of compound which is known in principle. Thus, 3-chloro-benzotriazine 1-oxide itself is obtained from 3-hydroxy-benzotriazine 1-oxide by reaction with boiling phosphorus oxychloride (J. Chem. Soc. 1957, 3186), and 3-bromo-benzotriazine 1-oxide is obtained in a corresponding manner with phosphorus oxybromide (see J. Org. Chem. 24, 813 (1959)). 3,7-Dichloro-benzotriazine 1-oxide and 3-chloro-7-methoxy-benzotriazine 1-oxide have already been prepared in an analogous manner (J. Org. Chem. 24, 813 (1959)). On the other hand, 3-chloro-benzotriazine 1-oxides with several chlorine atoms in the phenyl radical and with bromine, nitro or trifluoromethyl substituents have not hitherto been disclosed. The reason for this may be, in some cases, that the intermediate products required here cannot be prepared by the customary route without special measures.

The process known from the literature (Chem. Ber. 46, 3522 (1913); ibid. 50, 1248 (1917)) for the preparation of the 3-hydroxy-benzotriazine 1-oxides consists in either converting a 2-nitro-aniline (II), which may be additionally substituted, into the 2-nitro-phenyl isocyanate (III) with phosgene, converting this isocyanate into the 2-nitrophenylurea (IV) with ammonia and then cyclizing the urea by means of an alkali to give the 3-hydroxy-benzotriazine 1-oxide (V); or reacting the compound II with cyanamide to give the 2-nitrophenyl-guanidine (VI), cyclizing this compound in an alkaline medium to give the 3-amino-benzotriazine 1-oxide (VII) and then deaminating the product with nitrous acid to give (V) the 3-hydroxy-benzotriazine 1-oxide:

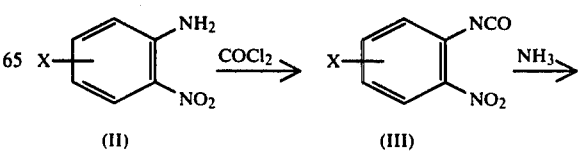

-continued

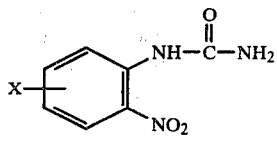

(IV)

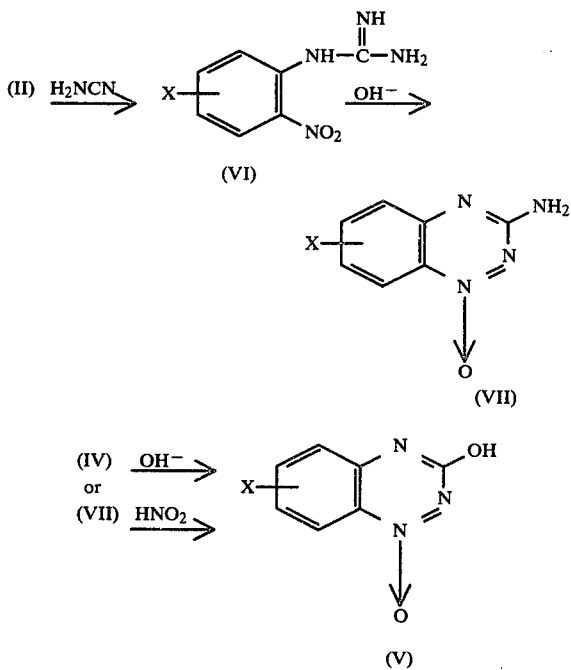

However, using customary methods, the phosgenation of the 2-nitro-anilines (II) to give the isocyanates (III), and also their reaction with cyanamide to give the guanidines (VI), fails if the molecule (II) contains, for example, more than one further halogen substituent or, for example, a further nitro group.

Thus, in order to prepare the isocyanates of the formula (III), which are not obtainable by the procedure indicated and are required as intermediate products, the phosgenation of the corresponding 2-nitroaniline of the formula (II) was carried out in phosphorus oxychloride as the reaction medium and not, as is otherwise customary, in hydrocarbons. The subsequent reaction to give the compounds of the formula (V), via the compounds of the formula (IV), then takes place in the customary manner.

Furthermore, the following process has also been found for the preparation of those 3-hydroxy-benzotriazine 1-oxides, required as starting materials, which have a nitro group in the 7-position (X in formula (V) in this case represents NO₂): the nitration of 3-hydroxy-benzotriazine 1-oxide is carried out with a nitric acid/sulphuric acid mixture in the temperature range between 0° and 25° C.:

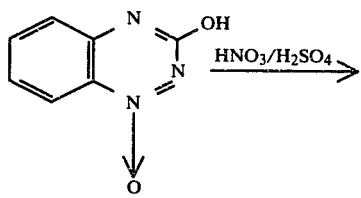

-continued

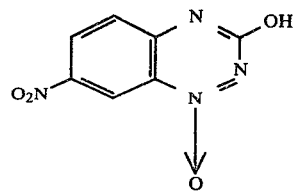

It is surprising that this nitration reaction is possible and leads to the 7-nitro compound in a simple and homogeneous manner, since according to the data in the literature, nitration of 3-hydroxy-benzotriazine 1-oxide should not be possible (J. Chem. Soc. 1957, 3186). The nitration proceeds quantitatively, for example, if it is carried out with a mixture of 28% of nitric acid (63% strength acid), 56% of concentrated sulphuric acid and 16% of water (so-called "mixed acid T").

As described above, the 3-halogeno-benzotriazine 1-oxides of the general formula (I) which can be used according to the invention may be prepared from the corresponding 3-hydroxy compounds of the formula (V) and a boiling phosphorus oxyhalide. However, in some cases the reaction proceeds unsatisfactorily. Relatively large amounts of by-products which are insoluble in organic solvents are usually formed even with a prolonged reaction time or another modification of the known reaction conditions. Even additions of up to molar amounts of phosphorus (V) halide do not produce better yields.

The present invention also provides a process for the preparation of a 3-halogeno-benzotriazine 1-oxide of the general formula (I) in which a 3-hydroxy-benzotriazine 1-oxide of the general formula

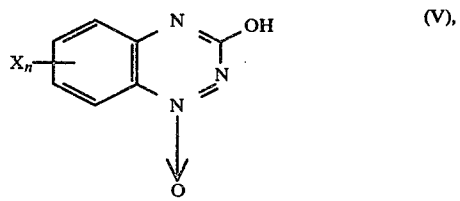

(V), in which

X and n have the meanings stated above, is reacted with a thionyl halide of the general formula SO(Hal)₂ (VI), in which Hal has the meaning stated above, in the presence of a carboxylic acid amide in the temperature range between +50° and 180° C.

The process, which is particularly suitable for the preparation of 3-chloro compounds (Hal thus preferably represents chlorine), has industrial advantages: in addition to the fact that insoluble by-products are avoided and the yield is increased, it has the advantage that aqueous working-up in order to isolate the compounds of the formula (I) is not necessary. In the case of the known use of a phosphorus oxyhalide as a reactant, polyphosphoric acid halides are unavoidably formed as byproducts and must be converted into (poly-)phosphoric acids by dissociation with water. If a thionyl halide is used, from which sulphur dioxide and a hydrogen halide are formed during the reaction, it is sufficient to distil off the excess of the thionyl halide. The separation of the reaction products (I) from the salt-like compounds formed from the catalyst (for example dimethylformamide) with the thionyl halide is effected in a simple manner by extraction with organic solvents, such as aliphatic and aromatic hydrocarbons and chlorohydrocarbons, or ethyl acetate.

If 3-hydroxy-7-chloro-benzotriazine 1-oxide and thionyl chloride are used as the starting materials, the course of the reaction can be represented by the following equation:

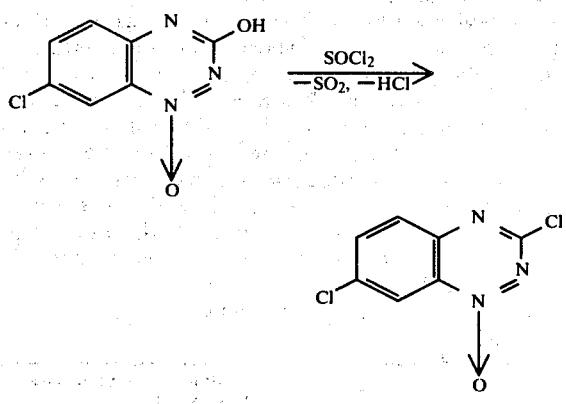

The reaction according to the invention is carried out in the presence of a carboxylic acid amide as a catalyst. In constrast to the known method, in accordance with which various hydroxy-N-heterocyclic compounds can also be converted into chloro-N-heterocyclic compounds by thionyl chloride, the procedure is different in the cases in which the 3-hydroxy-benzotriazine 1-oxides of the formula (V) are unsubstituted or monochloro-substituted in the phenyl radical: at least equimolar amounts of the catalyst, preferably dimethylformamide, are gradually added into the reaction mixture, which contains at least 2 mols of a thionyl halide per mol of hydroxy compound. It is surprising that high yields are achieved using this procedure, while only slight reactions can be detected with the known method (using only 0.01 to 0.1 mol of dimethylformamide). Moreover, it was surprising to establish that the amounts of catalyst of about 1 to 20 mol percent customarily used in the other types of reactions are sufficient if those 3-hydroxy-benzotriazine 1-oxides of the formula (V) which contain either several chlorine atoms or at least one bromine atom or one trifluoromethyl group or one nitro group as substituents in the phenyl radical are used as starting materials.

The thionyl halide required for the reaction according to the invention is used in excess; about 2 to 30 mols, preferably about 2 to 15 mols, of a thionyl halide, preferably thionyl chloride, are employed per mol of the hydroxy compound of the formula (V). The thionyl halide also simultaneously serves as the solvent. However, other solvents with a boiling point above about +60° C., for example carbon tetrachloride, toluene, nitrobenzene or chlorobenzene, can also be employed as diluents.

The reaction is carried out in the temperature range between about +50° and 180° C., preferably between about 75° and 150° C.

The following new compounds can be prepared by the process according to the invention: 3,6-dichlorobenzotriazine 1-oxide, 3,5,7-trichloro-benzotriazine 1-oxide, 3,6,7-trichloro-benzotriazine 1-oxide, 3-chloro-7-bromobenzotriazine 1-oxide, 3-chloro-7-phenoxy-benzotriazine 1-oxide, 3-chloro-7-trifluoromethyl-benzotriazine 1-oxide and 3-chloro-7-nitro-benzotriazine 1-oxide.

Further details of these can be found in the preparative examples given later in this text.

The active compounds which can be used according to the invention exhibit powerful bactericidal effects. They can be used as plant protection agents, for the treatment of above-ground parts of plants, for the treatment of seed and for the treatment of soil.

Bactericidal agents are employed in plant protection for combating bacteria from the family of the Pseudomonadaceae, for example *Pseudomonas solanacearum, Pseudomonas lachrymans, Pseudomonas syringae, Xanthomonas citri, Xanthomonas oryzae* and *Xanthomonas vesicatoria*, from the family of Enterobacteriaceae, for example *Erwinia amylovora* and from the family of the Corynebacteriaceae, and also from the family of the Rhizobiaceae, for example *Agrobacterium tumefaciens*.

The compounds which can be used according to the invention are well tolerated by plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The active compounds according to the invention can be present in the formulations as a mixture with other active compounds, such as fungicides, insecticides, acaricides, nematicides, herbicides, bird repellents, growth factors, plant nutrients and agents for improving soil structure.

The formulations in general contain from 0.1 to 95 percent by weight of active compound, preferably from 0.5 to 90 percent.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomizing, dusting, scattering, dry dressing, moist dressing, wet dressing, slurry dressing or encrusting.

Especially when they are used as leaf bactericides, the active compound concentrations in the use forms can be varied within a substantial range. They are, in general, from 0.5 to 0.0005 percent by weight, preferably from 0.2 to 0.001%.

For the treatment of seed, amounts of active compound of 0.01 to 50 g, preferably 0.5 to 5 g, are generally employed per kilogram of seed.

For the treatment of soil, amounts of active compound of 1 to 1,000 g, preferably of 10 to 200 g, are generally employed per cubic meter of soil.

The invention also provides crops protected from damage by bacteria by being grown in areas in which immediately prior to and/or during the time of the growing, a compound of the formula (I) was applied alone or in admixture with a diluent or carrier.

It will be seen that the usual methods of providing a harvested crop may be improved by the present invention.

The preparation of the active materials is shown in the following illustrative examples:

EXAMPLE 1

(a) Preparation of the precursors

2-Nitro-phenylureas of the general formula

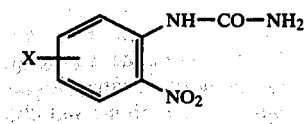

General Procedure:

Phosgene was condensed into 1,200 ml of phosphorus oxychloride, to which 5 ml of dimethylformamide had been added, for 6 hours at a temperature of 0° to 5° C. 1 mol of a 2-nitro-aniline was then introduced in portions at the same temperature. The mixture was warmed to the boil in the course of 3 hours, while passing further phosgene in, and boiled under reflux for a further 3 hours. The phosphorus oxychloride was then distilled off in vacuo. The crude 2-nitrophenyl isocyanate which remained was dissolved in 1 liter of toluene and insoluble constituents which remained were filtered off. Gaseous ammonia was passed into this solution at 20° to 25° C. until it was present in excess. The 2-nitro-phenylurea which thereby precipitated was filtered off, washed with water in order to remove salt-like concomitant substances and dried.

By this route, there were obtained:

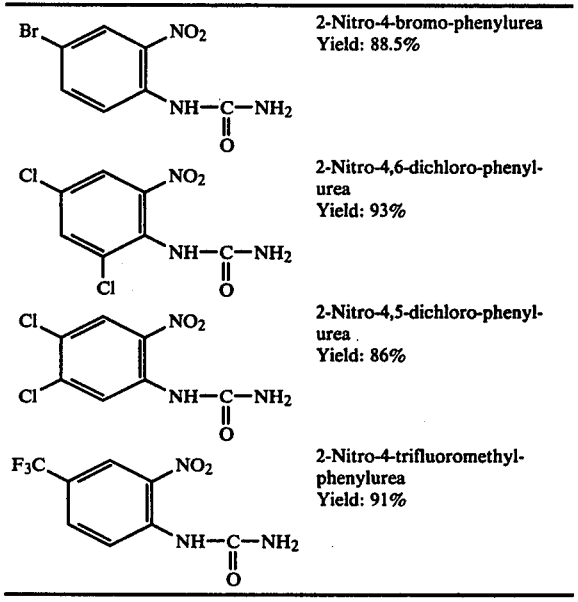

(b) 3-Hydroxy-benzotriazine 1-oxides of the general formula

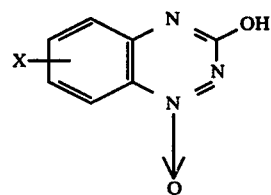

General Procedure:

1 mol of a 2-nitro-phenylurea was introduced in portions into a solution, warmed to 70° C., of 520 g of NaOH in 1.3 liters of water. The mixture was stirred at 70° C. for 2 hours, cooled to 50° to 60° C. and then acidified with hydrochloric acid. It was cooled further to room temperature and the reaction product was filtered off, washed several times with water and dried.

The following compounds of the formula (V) were obtained in this manner:

| X | Yield |
| --- | --- |
| H | 97% |
| 6-Cl | 81% |
| 7-Cl | 97% |
| 5,7-Di-Cl | 88% |
| 6,7-Di-Cl | 86% |
| 7-Br | 95% |
| 7-OCH₃ | 76% |
| 7-O-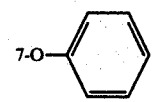 | 65% |
| 7-CF₃ | 82% | c)

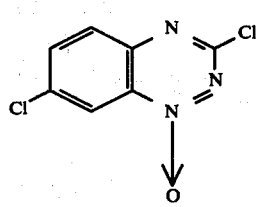 (1)

197.5 g (1 mol) of 3-hydroxy-7-chloro-benzotriazine 1-oxide were introduced in portions into 1 liter (about 1,655 g or 14 mol) of thionyl chloride. The mixture was heated to the boil and 116 ml (1.5 mol) of dimethylformamide were added dropwise in the course of 6 hours. After a clear solution had been formed, the mixture was kept at the boil for a further 2 hours and the excess thionyl chloride was then distilled off. The residue was stirred with 1 liter of toluene at 60° to 80° C. The insoluble constituents were filtered off and the toluene was evaporated off from the filtrate in vacuo. 175 g (81% of theory) of 3,7-dichloro-benzotriazine 1-oxide of melting point 157°–158° C. (recrystallized from wash benzine) were obtained as the residue.

The following compounds of the general formula

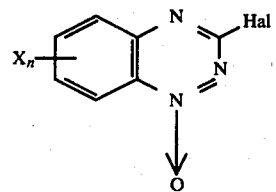 (I)

were prepared in a corresponding manner:

TABLE 1

| Compound No. | Xₙ | Hal | Yield (% of theory) | Melting point (°C.) |
| --- | --- | --- | --- | --- |
| 2 | 6-Cl | Cl | 78 | 159–161 |
| 3 | 7-CH₃O | Cl | 84 | 164–165 |
| 4 | 7-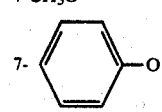-O | Cl | 57 | 182–183 |
| 5 | 5,7-Cl₂ | Cl | 92 | 129–130 |
| 6 | 6,7-Cl₂ | Cl | 80 | 112–113 |

EXAMPLE 2

(a) 3-Hydroxy-7-nitro-benzotriazine 1-oxide:

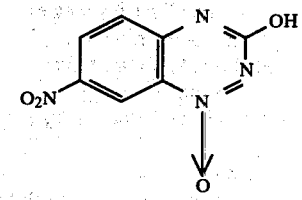

163 g (1 mol) of 3-hydroxy-benzotriazine 1-oxide were introduced in portions into 1.3 liters of a mixture of 28% of concentrated nitric acid (63% strength), 56% of concentrated sulphuric acid and 16% of water at 0° to 5° C., while stirring vigorously. The mixture was stirred for a further 1 hour, while cooling with ice, the temperature was allowed to rise to room temperature in the course of 2 hours and the mixture was subsequently stirred for a further 2 hours at room temperature. The reaction mixture was then stirred into 5 liters of ice-water and the crystals which thereby separated out were washed several times with water and dried. Yield: virtually quantitative. Melting point 214° C.

b)

(7)

208 g (1 mol) of 3-hydroxy-7-nitro-benzotriazine 1-oxide were introduced in portions into 1,400 ml (2,320 g or 19.5 mol) of thionyl chloride. 15 ml (0.2 mol) of dimethylformamide were then added and the mixture was heated to the boil until a clear solution had formed (about 4 to 6 hours). Working up was carried out as in Example 1. 195 g (86% of theory) of 3-chloro-7-nitro-benzotriazine 1-oxide of melting point 174°–175° C. (recrystallized from toluene) were obtained.

The following compounds of the general formula (I) were prepared in a corresponding manner:

TABLE 2

| Compound No. | Xₙ | Hal | Yield (% of theory) | Melting point (°C.) |
| --- | --- | --- | --- | --- |
| 8 | 7-CF₃ | Cl | 83 | 108–109 |
| 9 | 7-Br | Cl | 78 | 150–152 |

The bactericidal activity of the compounds of this invention is illustrated by the following examples wherein the compounds according to the present invention are each identified by the number (given in brackets) from the preparative examples hereinabove.

The known comparison compound is identified as follows:

(A)=3Cu(OH)₂.CuCl₃.×H₂O (copper oxychloride)

EXAMPLE 3

Agar plate test

Nutrient medium used:
20 parts by weight of agar-agar 200 parts by weight of potato decoction
5 parts by weight of malt
15 parts by weight of dextrose
5 parts by weight of peptone
2 parts by weight of disodium hydrogen phosphate
0.3 part by weight of calcium nitrate
Composition of the solvent mixture:
0.19 part by weight of acetone
0.01 part by weight of emulsifier (alkylaryl polyglycol ether)
1.80 parts by weight of water
Ratio of solvent mixture to nutrient medium:
2 parts by weight of solvent mixture
100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidified, the plates were inoculated with the species of organisms stated in the table and incubated at about 21° C.

Evaluation was carried out after 4–10 days, dependent upon the speed of growth of the organisms. When evaluation was carried out the radial growth of the organism on the treated nutrient media was compared with the growth on the control nutrient medium. In the evaluation of the organism growth, the following characteristic values were used:
1 no growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

70%, until they had dried. Needles were then dipped into an aqueous bacterial suspension of *Xanthomonas oryzae* and the plants were inoculated by pricking the leaves. After the inoculation, the leaves stood for 24 hours at 100% relative atmospheric humidity and thereafter in a room at 26° to 28° C. and 80% relative atmospheric humidity.

10 days after the inoculation, the infection of all pricked inoculated leaves of plants which had beforehand been treated with the preparation was evaluated, using a scale of from 1 to 9. 1 denoted 100% action, 3 denoted a good action, 5 denoted a moderate action and 9 denoted no action.

The active compounds, active compound concentrations and results can be seen from the table which follows:

TABLE 4

| | Bacteria test/*Xanthomonas oryzae* | |
|---|---|---|
| | Figure of merit of the infection, at an active compound concentration (in %) of | |
| Active compound | 0.025 | 0.05 |
| (A) | 7 | 5 |
| (2) | — | 3 |
| (8) | — | 3 |
| (1) | 3 | 3 |
| (7) | — | 3 |
| (5) | 3 | — |

It will be appreciated that the instant specification and examples are set forth by way of illustration and not limitation, and that various modifications and changes may be made without departing from the spirit and scope of the present invention.

What we claim is:

1. A method of combating plant-pathogenic bacteria which comprises applying to the bacteria, a bactericidally effective amount of a 3-halogeno-benzotriazine 1-oxide of the formula Table 3

| | | Agar plate test | | | | | |
|---|---|---|---|---|---|---|---|
| Active compounds | Active compound concentration [ppm] | *Pseudomonas lachrymans* | *Xanthomonas begoniae* | *Xanthomonas pelargonii* | *Erwinia carotovora* | *Erwinia mangiferae* | *Xanthomonas vesicatoria* |
| (A) | 50 | 9 | 5 | 5 | 5 | 3 | 9 |
| (2) | 50 | — | 2 | 3 | 1 | — | — |
| (1) | 50 | 1 | 1 | 1 | 1 | 1 | 2 |
| (6) | 50 | 2 | 1 | 2 | 1 | — | 5 |
| (9) | 50 | 1 | 1 | 1 | 1 | — | 5 |

EXAMPLE 4

Bacteria test/*Xanthomonas oryzae*

Solvent: 11.75 parts by weight of acetone
Dispersing agent: 0.75 part by weight of alkylaryl polyglycol ether
Water: 987.50 parts by weight The amount of active compound required for the desired active compound concentration in the spray liquor was mixed with the stated amount of the solvent and of the dispersing agent and the concentrate was diluted with the stated amount of water.

30 rice plants which were about 40 days old were sprayed with the spray liquor until dripping wet. The plants remained in a greenhouse, at temperatures of 22° to 24° C. and a relative atmospheric humidity of about in which
X each independently is halogen, a nitro group, an alkyl, halogenoalkyl, alkoxy, alkylmercapto or alkylsulphonyl group with up to 4 carbon atoms in each case, a phenoxy radical or a phenylmercapto radical,
n is an integer from 0 to 4, and
Hal is chlorine or bromine.

2. A method according to claim 1, in which
X each independently is chlorine, bromine, methoxy, phenoxy, methylmercapto, methyl, trifluoromethyl or nitro,
n is 0, 1 or 2, and
Hal is chlorine.

3. The method according to claim 1, wherein the 3-halogeno-benzotriazine 1-oxide is 3,7-dichloro-benzotriazine 1-oxide of the formula

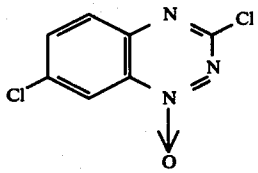

4. The method according to claim 1, wherein the 3-halogeno-benzotriazine 1-oxide is 3,6-dichloro-benzotriazine 1-oxide of the formula

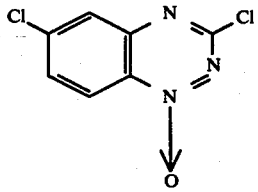

5. The method according to claim 1, wherein the 3-halogeno-benzotriazine 1-oxide is 3,5,7-trichloro-benzotriazine 1-oxide of the formula

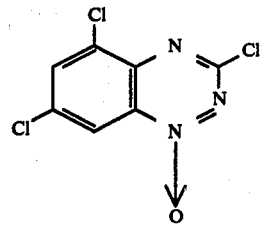

6. The method according to claim 1, wherein the 3-halogeno-benzotriazine 1-oxide is 3,6,7-trichloro-benzotriazine 1-oxide

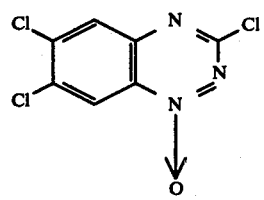

7. The method according to claim 1, wherein the 3-halogeno-benzotriazine 1-oxide is 3-chloro-7-bromo-benzotriazine 1-oxide of the formula

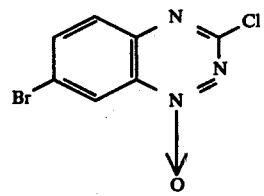

* * * * *